United States Patent [19]

Drake

[11] 4,053,515

[45] Oct. 11, 1977

[54] CATALYTIC HYDROGENATION OF UNSATURATED DINITRILES EMPLOYING HIGH PURITY ALUMINA

[75] Inventor: Charles A. Drake, Nowata, Okla.

[73] Assignee: Phillips Petroleum Company, Bartlesville, Okla.

[21] Appl. No.: 597,616

[22] Filed: July 21, 1975

Related U.S. Application Data

[63] Continuation-in-part of Ser. No. 416,784, Nov. 19, 1973, Pat. No. 3,896,173, and Ser. No. 416,785, Nov. 19, 1973, Pat. No. 3,896,174.

[51] Int. Cl.$^2$ .................. C07C 87/14; C07C 85/12
[52] U.S. Cl. .................. 260/583 P; 252/438; 252/440; 252/442; 252/466 R; 252/466 PT; 260/583 K; 260/677 H; 260/683.9; 260/690
[58] Field of Search .......... 260/583 K, 583 P, 677 H, 260/690; 252/442, 466 R, 466 PT, 463

[56] References Cited

U.S. PATENT DOCUMENTS

| | | | |
|---|---|---|---|
| 2,460,733 | 2/1949 | Bruson et al. | 260/583 K |
| 2,504,024 | 4/1950 | Howk et al. | 260/583 K |
| 2,606,925 | 8/1952 | Whitman | 260/563 |
| 2,781,399 | 2/1957 | Shapiro | 260/583 K |
| 2,956,075 | 10/1960 | Boffa et al. | 260/583 K X |
| 3,117,162 | 1/1964 | Rylander et al. | 260/583 K |
| 3,192,262 | 6/1965 | Schreyer | 260/563 |
| 3,244,644 | 4/1966 | Stiles | 252/466 |
| 3,372,195 | 3/1968 | Little | 260/570.7 |
| 3,408,397 | 10/1968 | Feldman et al. | 260/583 K |
| 3,471,563 | 10/1969 | Brake | 260/583 K |
| 3,488,390 | 1/1970 | Carss | 260/583 K |
| 3,536,632 | 10/1970 | Kroll | 252/430 |
| 3,558,709 | 1/1971 | Hockele | 260/583 K |
| 3,576,768 | 4/1971 | Kehl et al. | 252/465 |
| 3,880,928 | 4/1975 | Drake | 260/583 P |
| 3,896,174 | 7/1975 | Drake | 260/583 P |

OTHER PUBLICATIONS

"The Kirk-Othmer Encyclopedia of Chemical Technology", 2nd Edition, vol. 2, pp. 53–58 (1963).
Ham et al., "J. Org. Chem.", vol. 29, pp. 194–198 (1964).
Rylander, "Catalytic Hydrogenation Over Platsnum Metals", 114, Academic Press, N.Y. (1967).
Albisetti et al., "J. Am. Chem. Soc.", vol. 78, pp. 2637–2641 (1956).
Berkowitz et al., "J. Org. Chem.", vol. 24, pp. 708–709 (1959).
"The Catapal® Aluminas", Continental Oil Co. Brochure (1971).

Primary Examiner—Daniel E. Wyman
Assistant Examiner—John J. Doll

[57] ABSTRACT

The catalytic hydrogenation of an unsaturated dinitrile reactant of the formula

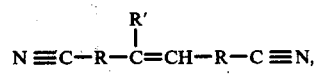

wherein each R is an alkylene or an alkylidene radical, and each R' is an alkyl radical, is carried out in the presence of a secondary amine formation suppressant, hydrogen, a suitable diluent, and a catalyst composed of a catalytic component supported on high purity alumina, the catalytic component being selected from ruthenium, rhodium, palladium, cobalt and nickel in element form or in the form of a compound which is reducible by hydrogen to the elemental metal.

20 Claims, No Drawings

CATALYTIC HYDROGENATION OF UNSATURATED DINITRILES EMPLOYING HIGH PURITY ALUMINA

This is a continuation-in-part of my copending application Ser. No. 416,784, filed Nov. 19, 1973, now U.S. Pat. No. 3,896,173, and my copending application Ser. No. 416,785, filed Nov. 19, 1973, now U.S. Pat. No. 3,896,174.

This invention relates to a process for the preparation of saturated aliphatic diamines by the catalytic hydrogenation of unsaturated aliphatic dinitriles.

In general, various processes for the catalytic hydrogenation of unsaturated aliphatic dinitriles to saturated aliphatic diamines are known to the art. Group VIII metal catalysts such as cobalt, nickel, ruthenium, rhodium, or palladium have been employed as effective catalysts for the hydrogenation of various feedstocks in these processes. However, it has been discovered that many of these hydrogenation catalyst materials are not always efficient or effective for the hydrogenation of unsaturated aliphatic dinitriles having the formula

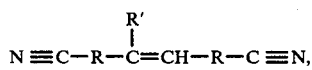

wherein each R is an alkylene or an alkylidene radical, and each R' is an alkyl radical. It has also been proposed to effect the hydrogenation of alkylene-substituted aliphatic dinitriles with a Group VIII metal catalyst in two stages, i.e. hydrogenation of the olefinic unsaturation in the first stage and hydrogenation of the nitrile unsaturation in a second subsequent stage, with ammonia being present only in the second stage. However, this proposal results in low yields of the desired product and high production of undesired heavy byproduct material.

In accordance with this invention these branched-chain unsaturated aliphatic dinitriles can be efficiently reduced to branched-chain saturated aliphatic diamines by the use of a catalyst compound of a catalytic component supported on high purity alumina, the catalytic component being selected from the group consisting of elemental ruthenium, elemental rhodium, elemental palladium, elemental cobalt, elemental nickel, and compounds of ruthenium, rhodium, palladium, cobalt or nickel which are reducible by hydrogen to the elemental form at the hydrogenation reaction conditions, and mixtures thereof, in the presence of hydrogen, a suitable diluent, and a secondary amine formation suppressant, e.g. ammonia. When the reaction is carried out in two stages, i.e. predominantly the hydrogenation of the nitrile unsaturation in a first stage and the hydrogenation of the olefinic unsaturation in a second stage, the ammonia will be present in the first stage reaction and absent from the second stage reaction.

It is an object of this invention to provide a process for the catalytic hydrogenation of branched-chain unsaturated aliphatic dinitriles to branched-chain saturated aliphatic diamines. Another object is to provide an efficient process for the catalytic hydrogenation of an unsaturated dinitrile having the formula

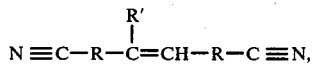

wherein each R is an alkylene or an alkylidene radical, and each R' is an alkyl radical. Still another object is to provide an efficient process for the catalytic hydrogenation of a mixture of branched-chain unsaturated aliphatic dinitriles to produce saturated aliphatic diamines. Still another object is to provide an efficient process for the catalytic hydrogenation of branched-chain unsaturated aliphatic dinitriles under reaction conditions which limit the occurrence of byproduct reactions. Other objects, aspects and advantages of the invention will be apparent from a study of the specification and the appended claims.

The branched-chain unsaturated aliphatic dinitriles which are considered to be advantageously and efficiently hydrogenated in accordance with the process of this invention are the unsaturated dinitriles of the formula

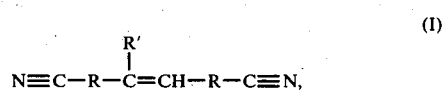

wherein each R is independently selected from the group consisting of an alkylene radical and an alkylidene radical, and R' is an alkyl radical. Each R will generally have from 1 to 15 carbon atoms, preferably from 1 to 6, and more preferably from 1 to 3 carbon atoms. R' will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 to 12 carbon atoms.

Representative of unsaturated reactant species of formula (I) include such compounds as 3-methyl-3-hexenedinitrile, 3-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures thereof.

If desired, other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

wherein each R'' is independently selected from the group consisting of an alkylene radical and an alkylidene radical. In general, each R'' will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 15-methylenenonacosanedinitrile, 12-methylenetetracosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the invention increase with increasing concentrations of the dinitriles of formula (I) in the feedstock. Thus, the process of the invention is even more advantageous for concentrations of the dinitriles of formula (I) in the feedstock of at least 5 weight percent. The invention is considered to be particularly desirable for dinitrile feedstocks having a concentration of the dinitriles of formula (I) of at least 10 weight percent.

A presently preferred branched-chain unsaturated aliphatic dinitrile feedstock for employment in the practice of this invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

In the practice of this invention, the catalytic hydrogenation of the unsaturated dinitrile reactant of formula (I) results primarily in the formation of saturated diamine reaction products having the formula

(III)

wherein R and R' are as defined hereinbefore. The catalytic hydrogenation of an unsaturated dinitrile reactant of formula (II) results primarily in the formation of saturated diamine reaction products having the formula

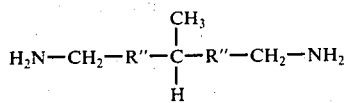

(IV)

wherein R" is as defined hereinbefore.

The practice of this invention is particularly suited to the catalytic hydrogenation of this mixture of species of formula (I) and formula (II) for the purpose of achieving saturated diamine reaction products which are substantially free of any olefinic unsaturation and preferably essentially free of any olefinic unsaturation. The phrase "substantially free of olefinic unsaturation" signifies that the diamine reaction products contain less than about 1 weight percent unsaturated diamine reaction product based on the total weight of unsaturated and saturated diamine reaction products wherein the weight percents are determined by conventional gas-liquid chromatographic analysis (GLC). The phrase "essentially free of olefinic unsaturation" signifies that the diamine reaction products contain less than about 0.1 weight percent unsaturated diamine reaction product based on the total weight of unsaturated and saturated diamine reaction products wherein the weight percents are determined by conventional GLC analysis techniques. These diamine reaction products which are at least substantially free, and preferably essentially free, of olefinic unsaturation are advantageously employed in the preparation of linear terephthalamide polymers.

One of the most important advantages of the catalytic hydrogenation process of this invention is directly related to the production of a mixture of diamines which are essentially free of olefinic unsaturation from the unsaturated dinitrile product mixture produced by the reaction of acrylonitrile and isobutylene. This advantage is significant since early prior art processes for the catalytic hydrogenation of the acrylonitrile and isobutylene reaction product mixture failed to substantially or completely reduce the olefinic unsaturation of the unsaturated dinitrile feedstock, thereby producing a reaction product mixture containing branched-chain aliphatic diamines having substantial olefinic unsaturation in the carbon skeleton. The separation of the branched-chain olefinically unsaturated diamines from the saturated diamines is inconvenient, and polyamides prepared from the mixtures containing a significant amount of unsaturated diamines have been found to be unsuited or undesirable in the preparation of polyamide fibers, particularly the terephthalamide polymers. Thus, the catalytic hydrogenation of this invention is a significant advance in the preparation of such polyamides.

The catalysts that are considered to be suitable for employment in the catalytic hydrogenation process of this invention are those catalysts composed of a catalytic component supported on high purity alumina, the alumina having a purity of at least 99.5, preferably at least 99.8, and more preferably at least 99.95 weight percent after calcining 3 hours at 482° C in the presence of hydrogen and in the absence of free oxygen. Suitable catalytic components include elemental ruthenium, elemental rhodium, elemental palladium, elemental cobalt, elemental nickel, compounds of ruthenium, rhodium, palladium, cobalt, or nickel which are reducible by hydrogen to finely divided elemental ruthenium, rhodium, palladium, cobalt, or nickel, and mixtures thereof. Suitable reducible compounds include the oxides, halides, nitrates, sulfates, oxalates, acetates, carbamates, propionates, tartrates, hydroxides, and the like, and mixtures thereof. Specific examples include ruthenium oxide, ruthenium chloride, ruthenium nitrate, ruthenium acetate, ruthenium carbonate, ruthenium hydroxide, rhodium oxide, rhodium chloride, rhodium nitrate, palladium oxide, palladium chloride, palladium nitrate, palladium acetate, Raney cobalt, cobalt oxide, cobalt chloride, cobalt nitrate, elemental nickel, Raney nickel, nickel oxide, nickel chloride, nickel nitrate, nickel oxalate, nickel acetate, and nickel hydroxide, and the like. Catalyst mixtures comprising any two or more of ruthenium, rhodium, palladium, cobalt and nickel can be employed in any weight ratio of one catalytic component to another without deleteriously affecting the catalytic hydrogenation benefits associated with the practice of this invention. The weight ratio of total catalytic component to unsaturated dinitrile reactant, based on the weight of the total of ruthenium, rhodium, palladium, cobalt and nickel contained therein, can be varied as desired. For the purpose of maintaining reasonable reaction rates under economically attractive catalyst reaction kinetics, it is generally preferred that the weight ratio of the total catalytic component to the unsaturated dinitrile reactants be maintained within a range of about 0.01:100 to about 30:100, and preferably in the range of about 0.1:100 to about 20:100.

The catalytic component can be added to the high purity alumina catalyst support by any of the methods well known in the art. For example, the supported catalysts can be prepared by dry mixing the components or by impregnating the support with a solution or dispersion of the catalytic component in elemental form or in the form of reducible compounds thereof. The supported catalyst can be calcined in the presence of hydrogen and in the absence of free oxygen to reduce the compounds, or such reduction can be achieved at the hydrogenation conditions employed in the hydrogenation reactor. The calcination of the supported catalyst can be conducted at any suitable conditions. In general the calcination is conducted at a temperature in the range of about 230° to about 500° C for a period of time in the range of about 0.5 hour to about 10 hours.

In a presently preferred embodiment of the invention the calcined supported catalyst is treated with an alkali metal hydroxide. This base treatment can be accomplished at any suitable conditions, but in general will be at a temperature in the range of about 0° to about 100° C for a period of time in the range of about 1 minute to 10 hours. The alkali metal hydroxide is preferably employed in the form of an aqueous solution containing from 0.5 weight percent alkali metal hydroxide up to the saturated concentration. Suitable alkali metal hydroxides include lithium hydroxide, sodium hydroxide, potassium hydroxide, and mixtures thereof. The treatment is carried out by contacting the calcined supported catalyst with the base solution and then rinsing the supported catalyst to remove excess base. Although the exact mechanism of the base treatment is not known, it is believed that the base treatment reduces the acid sites on the catalyst. The base treated catalyst is then calcined at suitable conditions under hydrogen and in the absence of free oxygen. In general the base treated catalyst will be calcined at a temperature in the range of about 230° C to about 500° C for a period of time in the range of 0.5 to 10 hours.

The elemental metal content of the catalytic component will generally be in the range of about 0.5 to about 50 weight percent, preferably in the range of about 1 to about 20 weight percent, based on the weight of the total of the catalytic component and the high purity alumina support. Presently preferred catalysts include ruthenium on high purity alumina, having a ruthenium metal content in the range of about 5 percent by weight, based on the total weight of the catalytic component and the support material, and nickel on high purity alumina, having a nickel metal content of about 15 to about 20 percent by weight, based on the weight of the total catalyst composition including the support.

While any alumina having a purity after calcination of at least 99.5, preferably at least 99.8, and more preferably at least 99.95, weight percent is considered suitable for use in the process of the invention, the presently preferred aluminas are the ultra high purity aluminas produced by the preparation of triethyl aluminum by the reaction of high purity aluminum, hydrogen and ethylene; the reaction of the resulting triethyl aluminum with additional ethylene molecules to form higher aluminum alkyls; oxidation of the aluminum alkyls to aluminum alkoxide; hydrolysis of the aluminum alkoxide to form an alumina slurry and alcohols; extraction of residual alcohols from the alumina slurry; and drying of the alumina. These ultra high purity aluminas are commercially available from the Continental Oil Company under the trademark CATAPAL. However, any process which produces a catalytic grade alumina with a purity of at least 99.5 weight percent (after calcination 3 hours at 482° C) and having a surface area of at least 1 $m^2/g$ is suitable. High purity gamma alumina is presently preferred.

Any catalytic hydrogenation temperature can be employed which provides the desired degree of catalytic efficiency in the hydrogenation of the branched-chain unsaturated aliphatic dinitrile containing feedstock. The hydrogenation temperatures will generally be within the range of about 30° to about 250° C. When two stages are employed, the hydrogenation temperatures in the first stage will generally be within the range of about 30° to about 200° C, and preferably will be within the range of about 70° to about 150° C. The hydrogenation temperature in the second stage will generally be within the range of about 100° to about 250° C and preferably will be within the range of about 125° to about 200° C.

The catalytic hydrogenation of branched-chain unsaturated aliphatic dinitriles can be carried out at any hydrogen pressure wherein both the olefinic unsaturation and the nitrile groups are reduced. Generally, suitable hydrogen pressures are within the range of from about 500 to about 5000 psig, but lower or even higher hydrogen pressures can be employed. Preferably, due to economic considerations, hydrogen pressures within the range of about 1000 to about 3000 psig are employed. Higher hydrogen pressures may be desirable at lower reaction temperatures in order to achieve complete reduction within a reasonable reaction time.

Any time interval suited for the catalytic hydrogenation of branched-chain unsaturated aliphatic dinitriles can be employed in the practice of this invention. However, time intervals economically attractive to the process are generally within the range of about 15 minutes to about 10 hours for a batch hydrogenation process. When two batch stages are employed, time intervals economically attractive to the process are generally within the range of about 15 minutes to about 5 hours for the first stage of a batch hydrogenation process, and generally within the range of about 15 minutes to about 5 hours for the second stage of the batch process. A total reaction time in the range of about 1 to about 6 hours is presently preferred in order to insure substantially complete hydrogenation of any unsaturated olefinic bonds in the feedstock as well as complete hydrogenation of the nitrile groups to primary amino groups. The catalytic hydrogenation of unsaturated dinitriles in accordance with the process of this invention can be carried out as a continuous process at any suitable liquid hourly space velocity (LHSV). However, the liquid hourly space velocity rates will generally be within the range of about 0.1 to about 10, more preferably from about 0.5 to about 2, volumes of unsaturated dinitrile reactant plus diluent per volume of catalyst (including the volume of the catalyst support) per hour.

While any suitable diluent can be employed in the process of this invention, the diluent will generally be selected from the class consisting of unsubstituted alkanols containing from 1 to 12 carbon atoms per molecule, unsubstituted acyclic and unsubstituted cyclic ethers having from 4 to 12 carbon atoms per molecule, and saturated hydrocarbons having 4 to 12 carbon atoms per molecule, and mixtures thereof. The term "unsubstituted" signifies that there are no substituents other than hydrocarbyl radicals. When a ruthenium catalyst is employed, it is preferred that the diluent be an unsubstituted alkanol or a saturated hydrocarbon. When a nickel catalyst is employed it is preferred that the diluent be one of said unsubstituted alkanols or one of said ethers. Examples of alkanol diluents include methanol, ethanol, 2-propanol, 2-methyl-2-propanol, 2-methyl-2-butanol, 2-butanol, 1-hexanol, 3-ethyl-3-hexanol, 2,4-dimethyl-2-pentanol, 2-decanol, 1-dodecanol, 2,3-dimethyl-3-pentanol, 3-ethyl-3-pentanol, 3,7-dimethyl-3-octanol, and the like, and mixtures thereof. The unsubstituted tertiary alkanols having at least 4 carbon atoms per molecule are the more preferred alkanol diluents. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures thereof. Examples of ethers include 1,3-dioxane, 1,4-dioxane, tetrahydrofuran, 4,4-dimethyl-1,3-dioxane, and mixtures thereof. To facilitate handling of the reaction mixtures, the weight ratio of unsaturated dinitrile reactants to diluent charged to the reaction zone is generally within the weight ratio range of about 0.001:100 to about 15:100, and is preferably in the range of about 0.1:100 to about 12:100.

A secondary amine formation suppressant, preferably ammonia, is employed in the single stage process and in the first stage (predominantly hydrogenation of the nitrile unsaturation) of the two-stage process of this invention as a means of suppressng undesirable side reactions such as the formation of secondary and tertiary amines. Any amount of secondary amine formation suppressant can be employed which is effective in deterring or reducing undesirable side reactions. In general, the mole ratio of secondary amine formation suppressant to cyano group (there being two cyano groups in each unsaturated dinitrile) will be in the range of about 1:1 to about 25:1, and preferably will be in the range of about 7:1 to about 15:1.

At the conclusion of the first stage reaction, the reactor is generally cooled to room temperature and then vented to allow essentially all of the ammonia to escape from the reactor. Although it will generally not be necessary, techniques other than venting can be employed in addition to or in lieu of venting to accomplish the removal of the ammonia. It is generally desirable that the level of ammonia be reduced to less than 5, and preferably less than 2, weight percent based on the unsaturated dinitrile in the charge to the first reaction stage, in order to minimize the effect of the ammonia on the catalyst activity. After the ammonia is vented, additional catalyst can be charged to the reactor, if desired. Such additional catalyst can be the same as the catalyst employed in the first stage reaction or it can be another suitable catalyst. Additional diluent is generally not required for the second stage reaction unless excessive diluent loss occurred during the removal of the ammonia. It is also within the scope of this invention to recover the product from the first reaction stage by separation of the same from the catalyst, diluent, and ammonia, and to utilize this product along with fresh catalyst and diluent as the charge to the second stage reaction.

Recovery of the desired end product, the branched-chain saturated aliphatic diamines, including preferred branched-chain saturated aliphatic diamine reaction products which contain less than about 0.1 percent unsaturated diamine by the weight of the total reaction product as determined by GLC, as well as any resulting reaction byproducts, any unconsumed reactants, ammonia, hydrogen, and/or diluents can be carried out by any conventional separation means. In general, at the conclusion of the catalytic hydrogenation process, the reaction effluent is cooled and depressurized with the recovery, if desired, of any ammonia, if any, or diluent which is vented from the reaction effluent during the depressurization operation. The ammonia or diluent can be returned or recycled to the hydrogenation zone if desired. The reaction products can be separated from the catalyst by conventional filtration means. The filtrate containing the at least substantially completely saturated diamines can be conveniently separated from any reaction byproducts or any diluent remaining in the filtrate by a conventional fractional distillation.

The following examples are presented in further illustration of the invention.

EXAMPLE I

Inventive and comparative nickel-containing hydrogenation catalysts used in this example were prepared by slurrying the appropriate alumina support in a solution of nickel nitrate hexahydrate in methanol such that the ratio of the weight of the alumina support to the weight of the nickel nitrate hexahydrate in the solution was 1:1. The methanol was stripped from the slurry under vacuum using a rotary evaporator and steam. The resultant solid was then treated as described in Table I.

Table I

| Catalyst | Treatment |
| --- | --- |
| A | Calcined under hydrogen at 600° F for 3 hours. Soaked in 5% aqueous NaOH for 5-10 minutes, then rinsed. Calcined under hydrogen at 600° F for 3 hours. |
| B | Calcined under hydrogen at 600° F for 3 hours. |
| C | Same as A except 2 hours for each calcination. |
| D | Calcined under hydrogen at 600° F for 2 hours. |
| E | Calcined under hydrogen at 800° F for 3 hours. |

The catalysts prepared as described above containing approximately 17 weight percent nickel were utilized in a series of runs for the catalytic hydrogenation of a mixture of olefinically unsaturated dinitriles prepared from isobutylene and acrylonitrile. The mixture contained approximately 52 weight percent 5-methylenenonanedinitrile, 35 weight percent 5-methyl-4-nonenedinitrile and other isomers in minor amounts.

In each run a solution of the above-described dinitrile mixture containing 8.3 weight percent dinitriles, 16.7 weight percent ammonia and 75 weight percent t- butanol was pumped at a rate of 1 ml/min through a 60 ml reactor packed with the appropriate catalyst under hydrogen at a pressure of 1500 psig. The effluent was analyzed directly by gas-liquid chromatography (GLC) for amount of unsaturated materials remaining and in some cases as noted the effluents collected over a 4-hour period were concentrated using a rotary evaporator and distilled. The resultant fractions were then analyzed by GLC. The results are tabulated in Table II.

Table II

| Run No. | Alumina[a] | Catalyst Treatment[a] | Temp.° C. | Product Sat'd Diamine /Heavies[b] | % Unsat'n[c] |
|---|---|---|---|---|---|
| 1 | HP[d] | A | 120 | [e] | 2 |
| 2 | " | A | 130 | [e] | 0 |
| 3 | " | A | 130 | 8.1 | 0 |
| 4 | " | A | 170 | 4.4 | 0 |
| 5 | " | B | 130 | 5.7 | 0 |
| 6 | " | B | 170 | 2.3 | 0 |
| 7 | NP[f] | C | 150 | [e] | 25 |
| 8 | " | C | 170 | 1.3 | [g] |
| 9 | " | D | 150 | [e] | 20 |
| 10 | " | E | 180 | [e] | 0 |
| 11 | " | B | 130 | 0.7 | 70[h] |
| 12 | " | B | 170 | 1.1 | [i] |

[a]Designations refer to Table I.
[b]Weight ratio of saturated diamine to undistilled heavies.
[c]Percent of original olefinic unsaturation remaining in reaction effluent.
[d]High purity alumina - 99.99% $Al_2O_3$ after calcining.
[e]Not determined.
[f]Normal purity alumina - contains 0.90% $Na_2O$, 0.08% $Fe_2O_3$, 0.09% $SiO_2$ and 6.5% volatiles before calcining.
[g]None detected until end of 4-hour run when low amount was observed.
[h]Also contains 40% of original nitrilic unsaturation.
[i]None detected until end of 4-hour run when 1% was observed.

The data in Table II show that hydrogenations of the dinitrile mixture conducted over nickel supported on high purity alumina proceeded to give higher ratio saturated diamine product to heavies and higher degree of hydrogenation than those conducted over nickel supported on alumina of lower purity under comparable conditions. The data in Table II also show that the base treatment of the high purity alumina further increases the ratio of saturated diamine to heavies compared to untreated high purity alumina under comparable conditions.

EXAMPLE II

Inventive and comparative ruthenium-containing hydrogenation catalysts used in this example were prepared by slurrying the appropriate alumina support in a solution of ruthenium trichloride hydrate dissolved in methanol (8.3 gm alumina per gram ruthenium trichloride hydrate). The methanol was stripped from the slurry under vacuum using a rotary evaporator and steam. A commercial catalyst containing 5 weight percent ruthenium on alumina was also employed as a comparative catalyst. The catalysts were calcined under hydrogen at 800° F for 3 hours prior to use.

In each run a one liter reactor was charged with 30 gm of the dinitrile mixture described in Example I, 276 gm t-butanol and one gram of the respective one of the above-described catalysts containing 5 weight percent ruthenium on the appropriate support. The reactor was then flushed with nitrogen, charged with 30 gm ammonia, pressurized to 1500 psig with hydrogen and heated at 170° C for 2 hours. Analysis of the resultant reaction mixtures by GLC yielded the results tabulated in Table III.

Table III

| Run No. | Catalyst Support | Reaction Mixture[a] Sat'd[b] Diamine | Unsat'd[c] Diamine | Amine-[d] Nitrile | Unsat'd[e] Dinitrile |
|---|---|---|---|---|---|
| 13 | HP | 100 | 0 | 0 | 0 |
| 14 | NP[f] | 10 | 20 | 30 | 40 |
| 15 | NP | 10 | 10 | 25 | 55 |

[a]Area percent of components eluted through gas chromatograph.
[b]Predominantly 5-methyl-1,9-nonanediamine.
[c]Olefinically unsaturated diamine.
[d]Olefinically unsaturated amine nitrile.
[e]Starting material.
[f]Commercially available 5% ruthenium on alumina.

These data illustrate that batch hydrogenation of the dinitrile mixture under otherwise comparable conditions proceeds to give completely saturated product with the inventive catalyst system and incompletely hydrogenated material with the prior art catalysts.

Reasonable variations and modifications are possible within the scope of the foregoing disclosure and the appended claims to the invention.

That which is claimed is:

1. A process for the catalytic hydrogenation of an unsaturated dinitrile feedstock comprising at least one unsaturated dinitrile compound of the formula

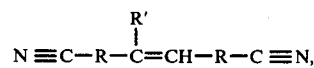

wherein each R is individually selected from the group consisting of an alkylene radical and an alkylidene radical, R' is an alkyl radical, and the number of carbon atoms in said compound is in the range of 7 to 30; which comprises contacting said feedstock under suitable hydrogenation conditions with a secondary amine formation suppressant, hydrogen, a suitable diluent, and a supported catalyst to thereby effect the at least substantially complete hydrogenation of said at least one unsaturated dinitrile compound to the corresponding branched-chain saturated aliphatic diamine; said supported catalyst comprising a catalytic component and a catalyst support, said catalyst support consisting essentially of alumina having a purity of at least 99.5 weight percent after calcination, said catalytic component being selected from the group consisting of elemental ruthenium, elemental rhodium, elemental palladium, elemental cobalt, elemental nickel and compounds of ruthenium, rhodium, palladium, cobalt or nickel which are reducible by hydrogen to the respective elemental metal at said hydrogenation conditions.

2. A process in accordance with claim 1, wherein said feedstock further comprises at least one unsaturated dinitrile reactant of the formula

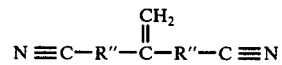

wherein each R" is independently selected from the group consisting of an alkylene radical and an alkylidene radical, and the number of carbon atoms in said reactant is in the range of 7 to 30.

3. A process in accordance with claim 1 wherein the content of the metal of said catalytic component is in the range of about 0.5 to about 50 weight percent of said supported catalyst.

4. A process in accordance with claim 1 wherein each of said alkylene radical, said alkylidene radical and said alkyl radical has from 1 to 15 carbon atoms.

5. A process in accordance with claim 1 wherein said at least one unsaturated dinitrile compound comprises 5-methyl-4-nonenedinitrile.

6. A process in accordance with claim 1 wherein said hydrogenation conditions comprise a weight ratio of the total catalytic component metal present to the unsaturated dinitriles in the range of about 0.01:100 to about 30:100, a mol ratio of secondary amine formation suppressant to cyano groups in the range of about 1:1 to about 25:1, a hydrogen pressure in the range of about 500 to about 5000 psig, a weight ratio of the unsaturated dinitriles to the diluent in the range of about 0.001:100 to about 15:100, a temperature in the range of about 30° to about 250° C, and a reaction time in the range of about 15 minutes to about 10 hours if conducted as a batch process and a liquid hourly space velocity rate in the range of about 0.1 to about 10 volumes of unsaturated dinitrile plus diluent per volume of catalyst if conducted as a continuous process.

7. A process in accordance with claim 2 wherein said hydrogenation conditions comprise a weight ratio of the total catalytic component metal present to the unsaturated dinitriles in a batch hydrogenation process in the range of about 0.1:100 to about 20:100 or a liquid hourly space velocity in the range of about 0.1 to about 10 volumes of unsaturated dinitrile reactant plus diluent per volume of total catalyst composition per hour in a continuous hydrogenation process; a mol ratio of ammonia to cyano groups in the range of about 7:1 to about 15:1, a hydrogen pressure in the range of about 1000 to about 3000 psig; and a weight ratio of the unsaturated dinitriles to the diluent in the range of about 0.1:100 to about 12:100.

8. A process in accordance with claim 7 wherein said catalytic component is selected from the group consisting of elemental ruthenium, ruthenium compounds which are reducible by hydrogen to elemental ruthenium at said hydrogenation conditions, and mixures thereof.

9. A process in accordance with claim 8 wherein said diluent is at least one member of the group consisting of tertiary alkanols and saturated hydrocarbons.

10. A process in accordance with claim 7 wherein said catalytic component is selected from the group consisting of elemental nickel, nickel compounds which are reducible by hydrogen to elemental nickel at said hydrogenation conditions, and mixtures thereof.

11. A process in accordance with claim 10 wherein said supported catalyst has been calcined, then treated with an alkali metal hydroxide, and the thus treated catalyst has been calcined before contacting said feedstock.

12. A process in accordance with claim 11 wherein said alkali metal hydroxide comprises sodium hydroxide.

13. A process in accordance with claim 1 wherein said supported catalyst has been calcined, then treated with an alkali metal hydroxide, and the thus treated catalyst has been calcined before contacting said feedstock.

14. A process in accordance with claim 13 wherein said alkali metal hydroxide comprises sodium hydroxide.

15. A process in accordance with claim 14 wherein said alumina has a purity of at least 99.8 weight percent.

16. A process in accordance with claim 1 wherein said alumina has a purity of at least 99.9 weight percent.

17. A process in accordance with claim 1 further comprising recovering a diamine product essentially free of unsaturation.

18. A process in accordance with claim 1 wherein said feedstock comprises 5-methylenenonanedinitrile and 5-methyl-4-nonenedinitrile.

19. A process in accordance with claim 1 wherein said catalyst support has been prepared by the preparation of triethyl aluminum by the reaction of high purity aluminum, hydrogen and ethylene; the reaction of the resulting triethyl aluminum with additional ethylene molecules to form higher aluminum alkyls; oxidation of the aluminum alkyls to aluminum alkoxide; hydrolysis of the aluminum alkoxide to form an alumina slurry and alcohols; extraction of residual alcohols from the alumina slurry; and drying of the alumina.

20. A process in accordance with claim 19 wherein said feedstock comprises 5-methylenenonanedinitrile and 5-methyl-4-nonenedinitrile.

* * * * *

UNITED STATES PATENT AND TRADEMARK OFFICE
CERTIFICATE OF CORRECTION

PATENT NO. : 4,053,515
DATED : October 11, 1977
INVENTOR(S) : Charles A. Drake

It is certified that error appears in the above-identified patent and that said Letters Patent are hereby corrected as shown below:

Column 12, line 24, delete "14" and insert -- 1 --.

Signed and Sealed this

Third Day of July 1979

[SEAL]

Attest:

Attesting Officer

LUTRELLE F. PARKER
Acting Commissioner of Patents and Trademarks